United States Patent [19]

Ando

[11] Patent Number: 4,759,347
[45] Date of Patent: Jul. 26, 1988

[54] ENDOSCOPE APPARATUS USING SOLID STATE IMAGE PICKUP DEVICE

[75] Inventor: Kunio Ando, Yono, Japan

[73] Assignee: Fuji Photo Optical Company, Ltd., Japan

[21] Appl. No.: 415,801

[22] Filed: Sep. 8, 1982

[30] Foreign Application Priority Data

Sep. 12, 1981 [JP] Japan ................. 56-144407
Sep. 12, 1981 [JP] Japan ................. 56-144408

[51] Int. Cl.$^4$ ............................................. A61B 1/06
[52] U.S. Cl. ............................................. 128/6; 358/98
[58] Field of Search ........................... 128/4–9, 128/23, 665; 358/42, 98, 110, 113, 253, 213; 362/32, 166–168, 293

[56] References Cited

U.S. PATENT DOCUMENTS

| | | | |
|---|---|---|---|
| 3,527,974 | 9/1970 | Cooper | 362/293 |
| 3,818,216 | 6/1974 | Larraburu | 362/293 |
| 3,936,147 | 2/1976 | Murakami . | |
| 4,016,598 | 4/1977 | Yamanaka . | |
| 4,074,306 | 2/1978 | Kakinuma et al. | 128/6 |
| 4,170,987 | 10/1979 | Anselmo et al. | 358/113 |
| 4,227,206 | 10/1980 | Nagumo . | |
| 4,242,700 | 12/1980 | Weimer | 358/213 |
| 4,253,447 | 3/1981 | Moore et al. . | |
| 4,261,344 | 4/1981 | Moore et al. . | |
| 4,345,269 | 8/1982 | Takemura . | |

FOREIGN PATENT DOCUMENTS 0055428 5/1977 Japan ................ 358/98

OTHER PUBLICATIONS

Japanese Unexamined Patent Publication No. 49, (1975)–114940.
Japanese Unexamined Patent Publication No. 51, (1976)–65962.

*Primary Examiner*—Max Hindenburg
*Attorney, Agent, or Firm*—Saidman, Sterne, Kessler & Goldstein

[57] ABSTRACT

An endoscope apparatus having an end section provided with an image forming optical system, a self-scanning type solid state image pickup device at which cyan and yellow color filters are positioned alternately to correspond to respective picture elements of the image pickup device, and a light guide. When green light is emitted from the light guide to an object, image signals corresponding to the green component of the object are picked up from all picture elements. When white light is emitted, cyan component image signals are picked up from the picture elements where the cyan filters are positioned, and yellow component signals form those where the yellow filters are positioned. Alternatively, when green light is emitted, green component signals are picked up from all picture elements and, when magenta light is emitted, blue component signals are picked up from the picture elements where the cyan filters are positioned and red component signals are picked up from those where the yellow filters are positioned. The image signals are then electrically processed to form a color image.

16 Claims, 3 Drawing Sheets

ENDOSCOPE APPARATUS USING SOLID STATE IMAGE PICKUP DEVICE

BACKGROUND OF THE INVENTION

1. Field of the Invention

This invention relates to an endoscope apparatus used for observation and recording of the interior of a section unobservable from the exterior, and more particularly to an endoscope apparatus provided with a solid state image pickup device.

2. Description of the Prior Art

In general, endoscopes, also called fiber scopes, are used to observe the interiors of body cavities or equipment and record images of the interiors. An end section of the fiber scope inserted into the interior to be observed includes an image forming optical system for forming an image of an object, one end of an optical fiber bundle called an image guide for transmitting the optical image created by the image forming optical system to the other end of the image guide, and one end of an optical fiber bundle called a light guide for illuminating the object. The optical image transmitted through the image guide is then enlarged by a loupe to facilitate observation, recorded on a photographic film or displayed by a CRT.

Recently, advances in semiconductor technology have led to the wide use of self-scanning type solid state image pickup devices, such as charge coupled devices (CCDs), and television cameras using solid state image pickup devices of this type have been put to practical use. The solid state image pickup devices of this type have an advantage over the image pickup tubes conventionally employed in television cameras, such as vidicons, in that they are smaller in size and lighter in weight. Under the above circumstances, it has been proposed in Japanese Unexamined Patent Publication Nos. 51(1976)-65962 and 49(1975)-114940 to incorporate a self-scanning type solid state image pickup device directly in in the above-described end section of an endoscope and convert the image of an object formed by the image forming optical system into an electric signal to display a television image on an image receiver (CRT display unit).

In general, to obtain a color television image on a CRT display unit, one of the image pickup systems described below will be employed. In the first and basic system, an image of an object formed by an image forming optical system is color-separated to red (R), green (G) and blue (B) color images, and three discrete solid state image pickup devices corresponding to the three primary colors are used. In the second system, only one solid state image pickup device is used, and red, green and blue primary-color filters are arranged in a mosaic form for respective picture elements of the solid state image pickup device to achieve multiplexing of the image pickup surface. In the third system, red, green and blue primary-color filters are rotated at a predetermined speed in front of a light source. The light source emits light to the illuminating member of the endoscope, i.e. the above-mentioned optical fiber bundle called a light guide, and the red, green and blue primary-color components of the image are picked up in a plane-sequential manner from a single solid image pickup device. However, these conventional systems present very real problems when used for endoscopes. Namely, the first system cannot be incorporated into a small and thin end section of an endoscope, although it is the most fundamental configuration and can provide good television images. If the first system is incorporated in the end section of an endoscope, the end section becomes large and the application range of the endoscope is limited. The second system can be incorporated in a small end section of an endoscope. However, in the second system, since the image pickup surface of the solid state image pickup device is color-separated by red, green and blue primary-color filters arranged in a mosaic form, the number of the picture elements for the green component that determines the resolving power is reduced, resulting in a drop in the resolving power. Particularly, when the end section of the endoscope is made small, it is difficult to use a solid state image pickup device having many picture elements. In this case, therefore, a reduction in the resolving power presents a very real problem. In the third system, since the three primary color components of the image are sequentially picked up by using a single solid state image pickup device in a plane-sequential mode, a problem concerning the timing of registration of the three primary color image arises for an object moving at a relatively high speed, resulting in deterioration of the image quality.

SUMMARY OF THE INVENTION

The primary object of the present invention is to provide an image pickup system suitable for an endoscope using a solid state image pickup device.

Another object of the present invention is to provide an endoscope apparatus having a small endoscope end section.

The specific object of the present invention is to provide an endoscope apparatus free from deterioration in resolving power and registration errors.

The present invention provides an endoscope apparatus using a solid state image pickup device, the endoscope apparatus comprising:

(a) an image forming optical system for forming an image of an object, (b) a self-scanning type solid state image pickup device for converting the image formed by said image forming optical system into an electric signal, and (c) an illuminating means for illuminating the object. These elements are positioned in an end section of the endoscope for insertion into a body cavity, the interior of a machine or the like. The solid state image pickup device is provided with cyan and yellow color filters alternately positioned to correspond to respective picture elements that make up the solid state image pickup device, whereby an image signal corresponding to the green component of the object is picked up from all picture elements of the solid state image pickup device when green light is emitted from the illuminating means to the object, an image signal corresponding to the cyan component of the object is picked up from the picture elements of the solid state image pickup device where the cyan color filters are positioned and an image signal corresponding to the yellow component of the object is picked up from the picture elements of the solid state image pickup device where said yellow color filters are positioned when white light is emitted from said illuminating means to the object, the image signals thereafter being electrically processed to form a color image. The color image signal obtained by electrically processing the image signals by an image signal processor is then displayed as a color image on a display unit such as a CRT display unit.

The present invention also provides an endoscope apparatus having the configuration described above, wherein an image signal corresponding to the green component of the object is picked up from all picture elements of the solid state image pickup device when green light is emitted from the illuminating means to the object and, when magenta light is emitted from the illuminating means to the object, an image signal corresponding to the blue component of the object is picked up from the picture elements of the solid state image pickup device where the cyan color filters are positioned and an image signal corresponding to the red component of the object is picked up from the picture elements of the solid state image pickup device where the yellow color filters are positoned, the image signals thereafter being electrically processed to form a color image.

The endoscope apparatus in accordance with the present invention is provided with only one solid state image pickup device, and yet achieves great improvements over the conventional systems with regard to resolving power and deterioration in image quality due to registration errors. Furthermore, the end section of the endoscope can be made small and, therefore, the apparatus is very advantageous particularly in applications where there is a limitation on the geometry and size of the end section.

DESCRIPTION OF THE PREFERRED EMBODIMENTS

The present invention will hereinbelow be described in further detail with reference to the accompanying drawings.

Figure 1:
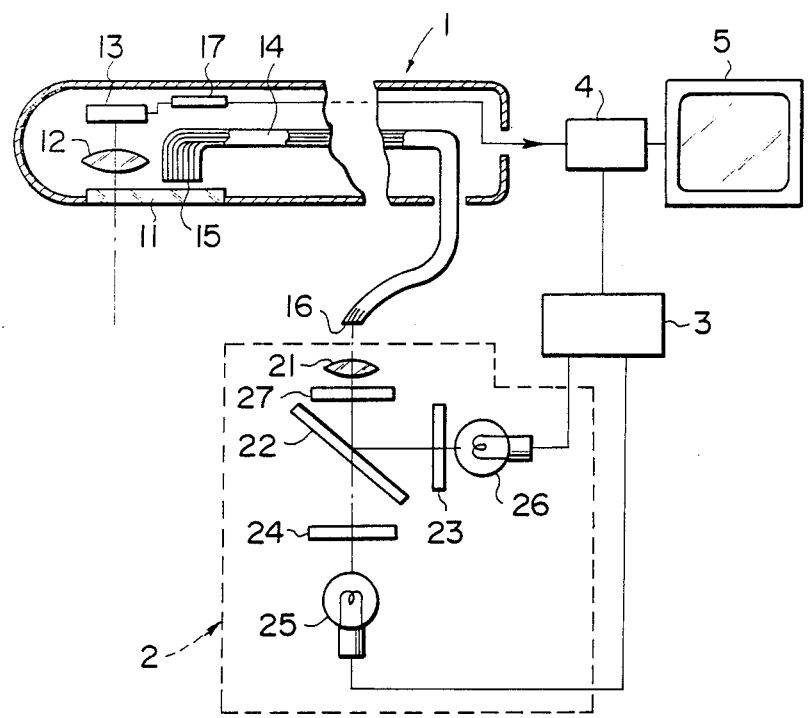
FIG. 1 is a schematic view showing an embodiment of the endoscope apparatus in accordance with the present invention.
Figure 2:
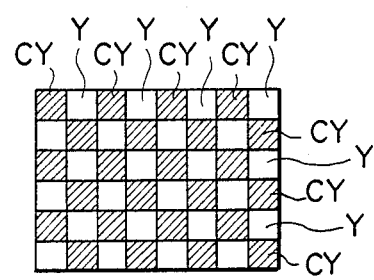
FIG. 2 is a plan view showing a mosaic filter employed in the apparatus shown in FIG. 1.

FIG. 1 schematically shows the approximate configuration of an embodiment of the endoscope apparatus in accordance with the present invention. In FIG. 1, the endoscope apparatus comprises an endoscope body 1, a light source unit 2, a synchronizing circuit 3, an image signal processing circuit 4 and an image display unit 5 such as a CRT display. In an end section of the endoscope body 1 to be inserted into an interior to be observed are incorporated at least an image forming optical system 12 for forming an image of an object in the interior, a self-scanning type solid state image pickup device 13 such as a CCD, and an end portion 15 of a light guide 14 serving as an illuminating member for illuminating the object. At the solid state image pickup device 13, cyan (CY) and yellow (Y) color filters are positioned in a mosaic form as shown in FIG. 2 so as to correspond to respective picture elements constituting the solid state image pickup device 13. The end section of the endoscope body 1 shown in FIG. 1 is also provided with a window glass 11, through which the image forming optical system 12 forms the image of an object on the image pickup surface of the solid state image pickup device 13. The end portion 15 of the light guide 14 emits light to the object throught the window glass 11. An electric image signal is obtained by the solid state image pickup device 13 and is sent throught a lead wire bundle 17 to the image signal processing circuit 4 and is then displayed as an image on the display unit 5. The lead wire bundle 17 includes lead wires for supplying clock signals used to drive the solid state image pick-up device 13, and the image signal processor 4 contains a circuit for feeding the clock signals to drive the CCD.

The light source unit 2 is provided with flash lamps 25 and 26 which can be alternately turned on and off at a high speed. A color temperature compensation filter 24 is positioned at the flash lamp 25, and a green filter 23 at the flash lamp 26. The green light and the white light emitted from these light sources are sent through a semi-transparent mirror 22 and an IR cut filter 27 and condensed on an end face 16 of the light guide 14 by a condenser lens 21. The flash lamps 25 and 26 are energized by a power source (not shown), and are alternately turned on and off in synchronized relation to respective fields of an image by the synchronizing circuit 3.

Figure 3:
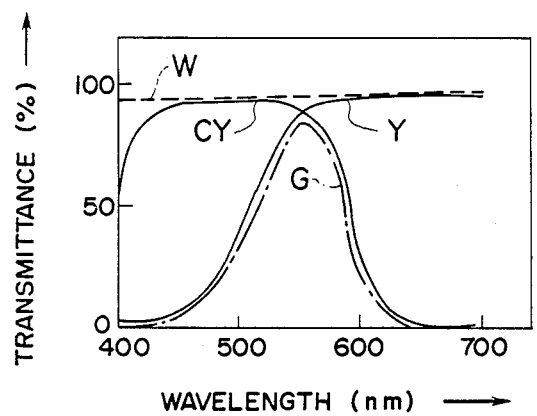
FIG. 3 is a graph showing the spectral transmittances of the cyan and yellow filters contained in the mosaic filter shown in FIG. 2 and the intensity of the green component light picked up by the cyan and yellow filters.

As described above, the cyan (CY) and yellow (Y) color filters shown in FIG. 2 are positioned at respective picture elements of the solid state image pickup device 13 shown in FIG. 1. Therefore, for example, when an odd image field (first field, third field, fifth field, . . .) is exposed to green light which exhibits the characteristics shown in FIG. 3 and which is generated by the flash lamp 26 and the green filter 23, the green component signal (G) of the object is picked up from both picture elements at which cyan filters are positioned and picture elements at which yellow filters are positioned, as shown in FIG. 3. Consequently, the green component signal of the object is picked up from all picture elements of the solid state image pickup device 13. Then, when an even image field (second field, fourth field, sixth field, . . .) is exposed to white light (W) (blue+green+red) which exhibits the characteristics shown in FIG. 3 and which is generated by the flash lamp 25 and the color temperature compensation filter 24, the cyan component signal (CY) of the object is picked up from the picture elements at which the cyan filters shown in FIG. 2 are positioned, and the yellow component signal (Y) of the object is picked up from the picture elements at which the yellow filters are positioned, as shown in FIG. 3. That is, the cyan and yellow component signals of the object are obtained from the even field. Thereafter, the green, cyan and yellow component signals are stored in a memory (buffer memory) contained in the signal processing circuit 4. A blue component signal is generated by subtracting the green component signal from the cyan component signal, and a red component signal is generated by subtracting the green component signal from the yellow component signal. In this way, television image signals are created by the signal processing circuit 4. In this case, the resolving power for the blue component signal and the red component signal of the object is one-half the resolving power for the green component signal. However, because the resolving power for the color television images is determined by the resolving power for the green component signal, the signal pick-up method described above does not adversely affect the color image resolving power. Furthermore, since signals of all color components of the object are obtained from two fields, the time required to obtain all color component signals is two-thirds the time required in the above-described conventional system for sequentially picking up the three-primary color image signals. Accordingly, the apparatus shown in FIG. 1 eliminates the problem concerning the timing of registration of three-primary color images, which arises in the third conventional system described above.

In the embodiment described above, the flash lamps that are turned on and off in synchronized relation to the fields are used as the light sources. However, it is also possible to use light sources in which green and magenta filters are rotated in synchronized relation to the fields. Furthermore, the mosaic filter comprising the cyan and yellow filters positioned in one-to-one relation to the respective picture elements of the solid state image pickup device may be replaced by a stripe filter provided with stripes extending vertically with respect to FIG. 2.

Figure 4:
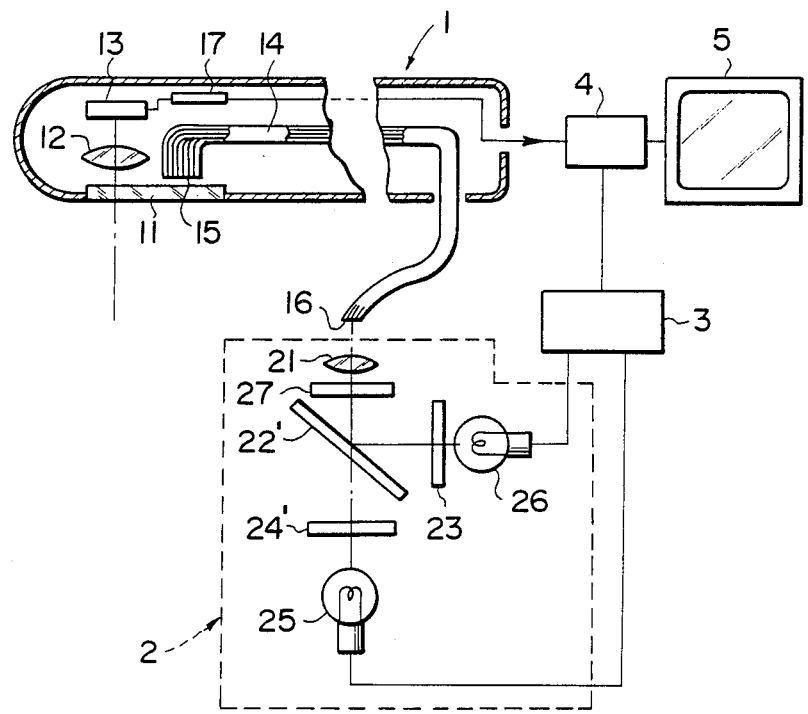
FIG. 4 is a schematic view showing another embodiment of the endoscope apparatus in accordance with the present invention.

FIG. 4 shows another embodiment of the endoscope apparatus in accordance with the present invention. In FIG. 4, similar elements are numbered with the same reference numerals as those in FIG. 1. The endoscope apparatus shown in FIG. 4 has the same configuration as that shown in FIG. 1, except that a magenta filter 24' is positioned at the flash lamp 25 instead of the color temperature compensation filter 24, and a dichroic mirror 22' capable of reflecting green light and transmitting magenta light is employed instead of the semitransparent mirror 22.

Figure 5:
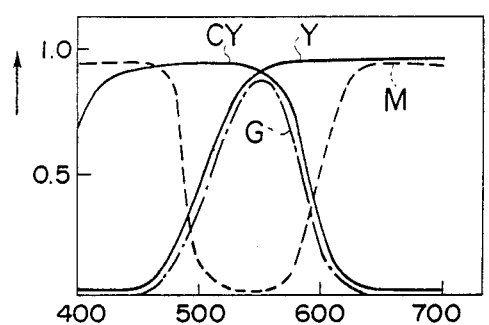
FIG. 5 is a graph showing the spectral distribution of source light containing green light and magenta light and the spectral transmittances of the cyan and yellow filters contained in the mosaic filter shown in FIG. 2.
Figure 6:
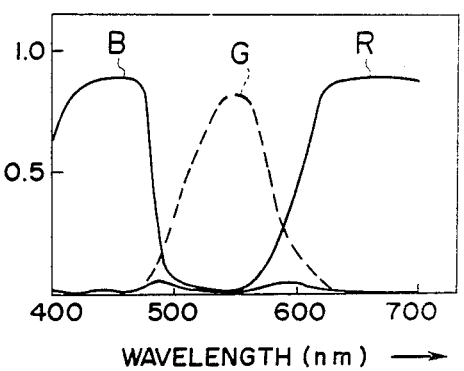
FIG. 6 is a graph showing the distribution of the color component light obtained by a combination of light source filters of FIG. 5.

In FIG. 4, the cyan (CY) and yellow (Y) color filters shown in FIG. 2 are positioned at respective picture elements of the solid state image pickup device 13 as described above with reference to FIG. 1. Therefore, for example, when an odd image field (first field, third field, fifth field, . . .) is exposed to green light which exhibits the characteristics shown in FIG. 5 and which is generated by the flash lamp 26 and the green filter 23, the green component signal (G) of the object as shown in FIG. 6 is picked up from both picture elements at which cyan filters are positioned and picture elements at which yellow filters are positioned, as shown in FIG. 5. Consequently, the green component signal of the object is picked up from all picture elements of the solid state image pickup device 13. Then, when an even image field (second field, fourth field, sixth field, . . .) is exposed to magenta light (M) which exhibits the characteristics shown in FIG. 5 and which is generated by the flash lamp 25 and the magenta filter 24', the blue component signal (B) of the object is picked up from the picture elements at which the cyan filters shown in FIG. 2 are positioned, and the red component signal (R) of the object is picked up from the picture elements at which the yellow filters are positioned, as shown in FIG. 6. That is, the blue and red component signals of the object are obtained from the even field. In this case, the resolving power for the blue component signal and the red component signal of the object is one-half the resolving power for the green component signal. However, the signal pick-up method conducted in the apparatus shown in FIG. 4 does not adversely affect the resolving power for the color television images as already described with reference to FIG. 1. Furthermore, the apparatus shown in FIG. 4 does not present the problem with regard to registration of three-primary color images because signals of all color components of the object are obtained from two fields and the time required to obtain all color component signals is two-thirds the time required in the third conventional system described above.

Figure 7:
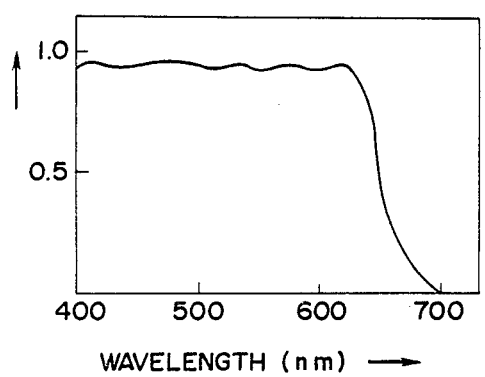
FIG. 7 is a graph showing the spectral transmittance of the IR cut filter employed in the apparatus shown in FIG. 4.
Figure 8:
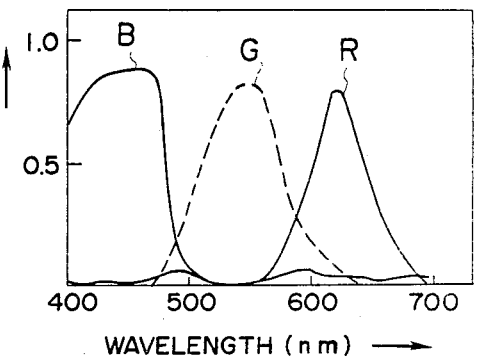
FIG. 8 is a graph showing the distribution of the color component light obtained by a combination of the light source filters of FIG. 5 and the IR cut filter exhibiting the spectral transmittance shown in FIG. 7.

As shown in FIG. 4, the IR cut filter 27 is positioned in the light source unit 2. The IR cut filter 27 may exhibit the spectral transmittance characteristics shown in FIG. 7. In this case, the spectral characteristics shown in FIG. 8 can be obtained by the combination of light source filters 23 and 24' exhibiting the characteristics shown in FIG. 5 and the IR cut filter 27 exhibiting the characteristics shown in FIG. 7. Accordingly, the apparatus shown in FIG. 4 can achieve excellent color reproduction.

Furthermore, the image signal processing circuit 4 may process the image signals in various ways. For example, the green image signals that are obtained from the odd fields, and the blue and red image signals that are obtained from the even fields may be alternately displayed for respective fields on a color television monitor. Alternatively, these image signals may be stored in a memory and called to respective fields of the color television monitor to process the image signals as simultaneous color image signals.

What is claimed is:

1. An endoscope for observing and recording an object in a body cavity or machine, the endoscope including an end section for insertion into the body cavity or machine, said end section comprising:
   (a) means for alternately illuminating the object with green light and white light;
   (b) an image-forming optical system for forming an image of the object;
   (c) a self-scanning solid state image pickup device having a plurality of picture elements for converting the image formed by said optical system into an electrical signal; and
   (d) cyan and yellow filters arranged in an alternating manner and positioned adjacent said plurality of picture elements, whereby:
      (i) when green light is emitted from said illuminating means to the object, an image signal corresponding to the green component of the object is picked up from all of said plurality of picture elements of said solid state image pickup device, and
      (ii) when white light is emitted from said illuminating means to the object, an image signal corresponding to the cyan component of the object is picked up from those of said plurality of picture elements where said cyan filters are positioned and an image signal corresponding to the yellow component of the object is picked up from those of said plurality of picture elements where said yellow filters are positioned.

2. An endoscope as defined in claim 1, further comprising an image signal processing circuit connected by a lead wire bundle to said pickup device.

3. An endoscope as defined in claim 2, further comprising a display unit connected to said processing circuit.

4. An endoscope as defined in claim 1, wherein said illuminating means comprises a light source unit essentially consisting of two flash lamps, a color temperature compensation filter positioned in front of one flash lamp, a green filter positioned in front of the other flash lamp, and a semitransparent mirror for directing both light from said color temperature compensation filter and light from said green filter towards said illuminating means.

5. An endoscope as defined in claim 4, wherein said light source unit further comprises an IR cut filter positioned to receive light from said semi-transparent mirror.

6. An endoscope as defined in claim 4, further comprising a synchronizing circuit connected to said flash lamps for alternately turning said flash lamps on and off in synchronized relation to respective image fields.

7. An endoscope for observing and recording an object in a body cavity or machine, the endoscope including an end section for insertion into the body cavity or machine, said end section comprising:
  (a) means for alternately illuminating the object with green light and magenta light;
  (b) an image-forming optical system for forming an image of the object;
  (c) a self-scanning solid state image pickup device having a plurality of picture elements for converting the image formed by said optical system into an electrical signal; and
  (d) cyan and yellow filters arranged in an alternating manner and positioned adjacent said plurality of picture elements, whereby:
    (i) when green light is emitted from said illuminating means to the object, an image signal corresponding to the green component of the object is picked up from all of said plurality of picture elements of said solid state image pickup device, and
    (ii) when magenta light is emitted from said illuminating means to the object, an image signal corresponding to the blue component of the object is picked up from those of said plurality of picture elements where said cyan filters are positioned and an image signal corresponding to the red component of the object is picked up from those of said plurality of picture elements where said yellow filters are positioned.

8. An endoscope as defined in claim 7, further comprising an image signal processing circuit connected by a lead wire bundle to said pickup device.

9. An endoscope as defined in claim 8, further comprising a display unit connected to said processing circuit.

10. An endoscope as defined in claim 7, wherein said illuminating means comprises a light source unit essentially consisting of two flash lamps, a magenta filter positioned in front of one flash lamp, a green filter positioned in front of the other flash lamp, and a dichroic mirror for directing both light from said magenta filter and light from said green filter towards said illuminating means.

11. An endoscope as defined in claim 10, wherein said light source unit further comprises an IR cut filter positioned to receive light from said dichroic mirror.

12. An endoscope as defined in claim 10, further comprising a synchronizing circuit connected to said flash lamps for alternately turning said flash lamps on and off in synchronized relation to respective image fields.

13. In an endoscope for observing and recording an object in a body cavity or machine, the endoscope including an end section for insertion into the body cavity or machine, the end section having means for illuminating the object, means for forming an image of the object, and a self-scanning solid state image pickup device having a plurality of picture elements for converting the image formed by the image forming means into an electrical signal, the method of forming a color image, comprising the steps of:
  (a) positioning alternating cyan filters and yellow filters adjacent the picture elements;
  (b) illuminating the object with green light and then detecting from all of the picture elements an image corresponding to the green component of the object;
  (c) illuminating the object with white light and then detecting from the picture elements having cyan and yellow filters, respectively, image signals corresponding to the cyan and yellow components, respectively, of the object; and
  (d) electrically processing the image signals to form the color image.

14. The method of claim 13, wherein said steps of illuminating the object with green light and white light comprise the steps of directing light from one flash lamp through a color compensation filter, directing light from another flash lamp through a green filter, and directing the output from said color compensation filter and said green filter to the object.

15. In an endoscope for observing and recording an object in a body cavity or machine, the endoscope including an end section for insertion into the body cavity or machine, the end section having means for illuminating the object, means for forming an image of the object, and a self-scanning solid state image pickup device having a plurality of picture elements for converting the image formed by the image forming means into an electrical signal, the method of forming a color image, comprising the steps of:
  (a) positioning alternating cyan filters and yellow filters adjacent the picture elements;
  (b) illuminating the object with green light and then detecting from all of the picture elements an image corresponding to the green component of the object;
  (c) illuminating the object with magenta light and then detecting from the picture elements having cyan and yellow filters, respectively, image signals corresponding to the blue and red components, respectively, of the object; and
  (d) electrically processing the image signals to form the color image.

16. The method of claim 15, wherein said steps of illuminating the object with green light and magenta light comprise the steps of directing light from one flash lamp through a magenta filter, directing light from another flash lamp through a green filter, and directing the output from said magenta filter and said green filter to the object.

* * * * *